United States Patent [19]

Araki et al.

[11] Patent Number: 4,495,283

[45] Date of Patent: Jan. 22, 1985

[54] PROCESS FOR PRODUCING L-HISTIDINE BY FERMENTATION

[75] Inventors: Kazumi Araki, Machida; Tetsuro Kuga, Komae, both of Japan

[73] Assignee: Kyowa Hakko Kogyo Co., Ltd., Tokyo, Japan

[21] Appl. No.: 482,892

[22] Filed: Apr. 7, 1983

[30] Foreign Application Priority Data

Apr. 10, 1982 [JP] Japan .................................. 57-59869

[51] Int. Cl.³ .................... C12P 13/24; C12N 15/00; C12N 1/20; C12R 1/13; C12R 1/15
[52] U.S. Cl. ................................ 435/107; 435/172.1; 435/840; 435/843; 435/253
[58] Field of Search ............. 435/107, 840, 843, 172.1

[56] References Cited

U.S. PATENT DOCUMENTS 3,713,977  1/1973  Nakayama et al. ................ 435/107
3,816,258  6/1974  Arai et al. ........................ 435/107
3,875,001  4/1975  Kubota et al. .................... 435/107

*Primary Examiner*—Lionel M. Shapiro
*Attorney, Agent, or Firm*—Fitzpatrick, Cella, Harper & Scinto

[57] ABSTRACT

L-histidine is produced by culturing, in a nutrient medium, an L-histidine producing mutant microorganism belonging to the genus Corynebacterium or Brevibacterium. The mutant is resistant to growth inhibition by an RNA polymerase inhibitor or requires adenine. L-histidine is accumulated in the culture liquor and is recovered therefrom.

9 Claims, No Drawings

PROCESS FOR PRODUCING L-HISTIDINE BY FERMENTATION

BACKGROUND OF THE INVENTION

The present invention relates to a process for producing L-histidine by fermentation, and more specifically to a process for producing L-histidine by culturing an L-histidine producing mutant microorganism belonging to the genus Corynebacterium or Brevibacterium in a nutrient medium and recovering the L-histidine produced thereby. The mutants employed are endowed with a resistance to growth inhibition by RNA polymerase inhibitors or a requirement for adenine.

L-histidine is an important amino acid which is commercially useful as a food additive or medicament. Accordingly, it is an object of the present invention to provide an improved process for production of such amino acid on an industrial scale at low cost.

Heretofore, it has been known that histidine analog-resistant strains belonging to the genus Corynebacterium or Brevibacterium have an ability to produce a significant amount of L-histidine (U.S. Pat. No. 3,713,977). Attempts to increase the productivity of these L-histidine producing microorganisms by imparting additional properties to them have also been made. For example, a process using strains endowed with a resistance to a purine analog or a pyrimidine analog is proposed in Japanese Published Examined Patent application No. 18798/1977. Another process using strains endowed with a requirement for arginine, methionine, tryptophan, phenylalanine, tyrosine, leucine, lysine or uracil is disclosed in U.S. Pat. No. 3,875,001. A further process using strains endowed with a resistance to sulfa drugs is disclosed in Japanese Published Unexamined Patent application No. 49490/1975. Yet another process using strains endowed with a resistance to 5-methyl-tryptophane, α-amino- β-hydroxyvaleric acid, imidazole or aminotriazole is proposed in Japanese Published Unexamined Patent application No. 49491/1975. In Japanese Published Unexamined Patent application No. 69292/1975, a process is proposed using strains endowed with a requirement for threonine, proline, shikimic acid, xanthine or guanine. Furthermore, a process using strains endowed with a resistance to cobalamine is disclosed in Japanese Published Unexamined Patent application No. 70591/1975.

Although the processes exemplified above result in improved yields of L-histidine, the production yields of such processes, nevertheless, are comparatively low from a commercial application standpoint. Thus, a need exists for a process for producing L-histidine in higher yields at low cost.

To this end, it has now been found that L-histidine productivity of an L-histidine producing microorganism belonging to the genus Corynebacterium or Brevibacterium is greatly improved when such microorganism is endowed with a resistance to growth inhibition by RNA polymerase inhibitors or a requirement for adenine. Heretofore, it was not recognized that the productivity of L-histidine could be improved by endowing an L-histidine producing microorganism with either of such traits.

SUMMARY OF THE INVENTION

In accordance with the present invention, L-histidine is produced by culturing an L-histidine producing mutant microorganism belonging to the genus Corynebacterium or Brevibacterium in a nutrient medium until L-histidine is accumulated in the culture liquor and thereafter recovering said L-histidine, wherein the mutant is characterized by a resistance to growth inhibition by RNA polymerase inhibitors or a requirement for adenine.

As used herein the term "resistance to growth inhibition by RNA polymerase inhibitors" means that the mutant is capable of growing in an nutrient medium containing an RNA polymerase inhibitor in an amount which would inhibit growth of the parent strain. Similarly, as used herein, the term "requirement for adenine" means that the mutant requires the presence of adenine in the nutrient medium for growth or growth comparable to its parent strain.

DESCRIPTION OF THE INVENTION

The microorganism utilized in the present invention is a mutant belonging to the genus Corynebacterium or Brevibacterium which has the ability to produce L-histidine and which has been endowed with a resistance to RNA polymerase inhibitors or a requirement for adenine. A suitable mutant may be obtained by using a mutant inherently having an ability to produce L-histidine (for example, histidine analog-resistant strains and sulfa drug-resistant strains) or an improved mutant thereof as a parent strain and imparting a resistance to at least one RNA polymerase inhibitor, e.g., rifamycin, streptovaricin, rifampicin, streptolydigin, actinomycin, chromomycin, daunomycin, adriamycin, pluramycin, kanchanomycin, echinomycin, or formycin or imparting a requirement for adenine to it. Alternatively, a suitable mutant may be prepared by a reverse process, i.e. by imparting the above-mentioned ability to produce L-histidine to a mutant resistant to RNA polymerase inhibitors or an adenine-requiring mutant. Moroever, as the strain used in this invention, a mutant having other properties such as various nutrient requirements, drug resistance, drug sensitivity and drug dependence in addition to a combination of the above properties may be employed.

Strains mutated as above mentioned are screened by culturing in a nutrient medium and a strain having the ability to produce L-histidine in greater yields than its parent strain is selected and used in this invention. A specific example of the procedure for obtaining a suitable strain is given in the following description with reference to a mutant belong to the genus Corynebacterium.

PROCEDURE

Corynebacterium glutamicum ATCC 13032 is mutated in a conventional manner using N-methyl-N'-nitro-N-nitro-soguanidine and strains resistant to an L-histidine analog, 2-thiazolealanine, are selected using conventional techniques. Then, via a culturing test, an L-histidine producing strain, for example, ATCC 21607 (2-thiazolealanine- resistant strain) is selected. Using the ATCC 21607 strain as the parent strain, mutation treatment and L-histidine production test are conducted to obtain an L-histidine producing strain, GAUPTr-113 (FERM P-1874) which has been successively endowed with 2-thiazolealanine resistance, 6-mercaptoguanine resistance, 6-azaguanine resistance, 6-azauracil resistance, 6-methylpurine resistance and 5-methyltryptophane resistance. The process for inducing a mutant of this type is also described in Japanese Published Examined Patent application No. 18798/1977.

A cell suspension of the foregoing mutant is cultured on an agar medium (0.5 g/dl yeast extract, 0.7 g/dl meat extract, 1 g/dl peptone, 0.3 g/dl NaCl, pH 7.0, 2 g/dl agar) containing 100 μg/ml rifampicin which is an RNA polymerase inhibitor by inoculating $10^7$ cells of the strain per plate and incubating at 30° C. for 2–3 days. Then 50 colonies of rifampicin-resistant cells are collected, and subjected to an L-histidine production test in the same manner as in the following Example 1 and mutants having a significantly improved ability to produce L-histidine compared with the simultaneously tested parent strain (GAUPTr-113) are separated. A representative strain among the thus obtained mutants was named 2R-18.

In a similar manner, from a 2-fluorohistidine-resistant and L-histidine producing strain B-39 (FERM P-6228) derived from Brevibacterium species ATCC 14902, a rifampicin-resistant mutant, BR-6, was prepared.

Similarly, an adenine-requiring mutant, HDA-5, was obtained by mutating the GAUPTr-113 strain and selecting a L-histidine producing and adenine requiring strain.

The aforesaid *Corynebacterium glutamicum* 2R-18, *Corynebacterium glutamicum* HDA-5 and Brevibacterium species BR-6 mutants were deposited on Mar. 26, 1982 with the Fermentation Research Institute, the Agency of Industrial Science and Technology, Japan as FERM BP-240, 241 and 242 respectively and are available therefrom under the terms of the Budapest Treaty.

As the medium used for the culturing step of the invention, either a natural medium or synthetic medium may be employed as long as it contains assimilable carbon sources, nitrogen sources and inorganic materials as well as small quantities of other nutrients which may be required by the specific mutant used. Typical additional nutrients are those employed in the following examples. As a suitable carbon source, carbohydrates such as sucrose, fructose, glucose, maltose, mannose, starch, starch hydrolyzate, molasses, etc.; sugar alcohols such as glycerine, sorbitol, etc.; organic acids such as formic acid, acetic acid, lactic acid, fumaric acid, malic acid, etc.; lower alcohols such as ethanol, methanol, etc., and the like may be employed. These carbon sources may be employed either alone or as a mixture at various weight ratios. The total amount may be initially supplied in the medium or may be supplied by incremental addition.

As the nitrogen source, various inorganic and organic ammonium salts such as ammonium chloride, ammonia, ammonium sulfate, ammonium carbonate, ammonium acetate, ammonium nitrate, ammonium phosphate, etc.; urea; natural nitrogen containing substances such as peptone, meat extract, corn steep liquor, casein hydrolyzate, soybean meal hydrolyzate, etc. and the like may be employed. As the inorganic materials, potassium dihydrogen phosphate, dipotassium hydrogen phosphate, magnesium sulfate, sodium chloride, ferrous sulfate, manganese sulfate, calcium carbonate, etc. are employed.

When the strain used requires nutrients such as amino acids, nucleic acids, vitamins, and the like, it is, of course, also necessary to include appropriate amounts of these substances to the medium. In some cases, such nutrients may be supplied by another medium component and thus specific supplementation is not required.

Culturing is generally carried out at 20°–40° C., under aerobic conditions, for example, by shaking culture or aeration agitation culture until recoverable quantities of L-histidine is produced in the culture liquor, usually within 1–8 days. After the completion of culturing, L-histidine is recovered from the culture liquor by a conventional method such as ion exchange resin treatment or the like.

Practice of certain specific embodiments of the invention is illustrated by the following representative examples.

EXAMPLE 1

In this example, *Corynebacterium glutamicum* 2R-18 (FERM BP-240) was employed as a seed strain. The seed strain was cultured with shaking in a medium having a composition of 4 g/dl glucose, 2 g/dl polypeptone, 0.15 g/dl $KH_2OP_4$, 0.05 g/dl $K_2HPO_4$, 0.05 g/dl $MgSO_4.7H_2O$, 50 μg/l biotin, 0.3 g/dl urea and 0.5 g/dl yeast extract (pH 7.2) at 30° C. for 24 hours. Then, 1 ml of the resulting seed culture was transferred to a 250 ml-Erlenmeyer flask containing 20 ml of a fermentation medium comprising 7 g/dl waste molasses (calculated as glucose), 0.5 g/dl meat extract, 4 g/dl $(NH_4)_2SO_4$, 0.15 g/dl $KH_2PO_4$, 0.05 g/dl $K_2HPO_4$, 0.05 g/dl $MgSO_4.7H_2O$, 0.3 g/dl urea and 3 g/dl $CaCO_3$ (pH 7.4) and cultured with shaking at 30° C. for 4 days. The amount of L-histidine produced was 10.5 mg/ml.

When the parent strain, GAUPTr-113, was cultured under the same conditions as a control, the amount of L-histidine accumulated was 8.9 mg/ml.

EXAMPLE 2

In this example, the L-histidine production test was conducted in the same manner as in Example 1 except that *Corynebacterium glutamicum* HDA-5 (FERM BP-241) was used as a seed strain and 150 μg/ml adenine was added to the fermentation medium. As a result, 9.7 mg/ml L-histidine was accumulated in the culture liquor.

The amount of L-histidine accumulated by culturing the parent strain, GAUPTr-113, under the same conditions as a control was 8.7 mg/ml.

EXAMPLE 3

In this example, similar procedures as in Example 1 were conducted except that Brevibacterium species BR-6 (FERM BP-242) was used as the seed strain. As a result, 4.3 mg/ml L-histidine was accumulated, whereas, the amount of L-hidtidine accumulated by the parent strain, B-39, was 2.9 mg/ml.

What is claimed is:

1. A process for producing L-histidine by fermentation which comprises culturing an L-histidine producing mutant microorganism belonging to the genus Corynebacterium or Brevibacterium in a nutrient medium until L-histidine is accumulated in the culture liquor and thereafter recovering said L-histidine therefrom; said mutant being characterized by at least a resistance to growth inhibition by an RNA polymerase inhibitor or a requirement for adenine.

2. A process according to claim 1 wherein said mutant is resistant to growth inhibition by an RNA polymerase inhibitor selected from the group consisting of rifamycin, streptovaricin, rifampicin, streptolydigin, actinomycin, chromomycin, daunomycin, adriamycin, pluramycin, kanchanomycin, echinomycin and formycin.

3. A process according to claim 1 wherein said culturing step is carried out at 20° to 40° C. for 1 to 8 days.

4. A process according to claim 1 wherein said microorganism has the identifying characteristics of *Corynebacterium glutamicum* 2R-18, FERM BP-240.

5. A process according to claim 1 wherein said microorganism has the identifying characteristics of *Corynebacterium glutamicum* HDA-5, FERM BP-241.

6. A process according to claim 1 wherein said microorganism has the identifying characteristics of Brevibacterium sp. BR-6, FERM BP-242.

7. A biologically pure culture of *Corynebacterium glutamicum* having the identifying characteristics of FERM BP-240, which produces recoverable quantities of L-histidine when cultured.

8. A biologically pure culture of *Corynebacterium glutamicum* having the identifying characteristics of FERM BP-241, which produces recoverable quantities of L-histidine when cultured.

9. A biologically pure culture of Brevibacterium sp. having the identifying characteristics of FERM BP-242, which produces recoverable quantities of L-histidine when cultured.

* * * * *